United States Patent [19]

Bondar et al.

[11] 3,991,086

[45] Nov. 9, 1976

[54] METHOD FOR PREPARING HIGHER BRANCHED UNSATURATED DIALKYLAMINO ACIDS

[76] Inventors: Ljudmila Sergeevna Bondar, ulitsa Obrucheva, 18, kv. 20; Rostan Alexandrovich Okunev, Novo-Basmannaya ulitsa, 4/6, kv. 162, both of Moscow, U.S.S.R.

[22] Filed: Oct. 6, 1975

[21] Appl. No.: 620,118

Related U.S. Application Data

[60] Continuation of Ser. No. 488,975, July 16, 1974, abandoned, which is a division of Ser. No. 193,211, Oct. 27, 1971, Pat. No. 3,840,571.

[52] U.S. Cl. .......................... 260/404; 260/482 P; 260/485 R; 260/534 E
[51] Int. Cl.² ........................................ C07C 101/20
[58] Field of Search .................................. 260/404

[56] References Cited
UNITED STATES PATENTS 3,517,041   6/1970   Scharr et al. .................... 260/448.2

OTHER PUBLICATIONS

Chem. Abstracts 37, 871[9] (1943).
Chem. Abstracts 44, 3080a (1950).
Chem. Abstracts 64, 110800f (1966).
Organic Reactions, vol. IX, Wiley & Sons, N.Y., pp. 175, 186, 196.
Chem. Abstracts 53, 21788–21789 (1959).
Chem. Abstracts 61, 13186 (1964).

*Primary Examiner*—Helen M. McCarthy
*Attorney, Agent, or Firm*—Holman & Stern

[57] ABSTRACT

Dialkylaminoalkylterpenylacetic acids prepared through the interaction of a terpenylmalonic or dialkylaminoalkylmalonic ester with a corresponding alkyl halide with subsequent saponification of the reaction mixture with a solution of an alkali in alcohol and decarboxylation in vacuum or in a medium of an inert high-boiling solvent.

14 Claims, No Drawings

METHOD FOR PREPARING HIGHER BRANCHED UNSATURATED DIALKYLAMINO ACIDS

This is a continuation of application Ser. No. 488,975 filed July 16, 1974 now abandoned, which in turn is a divisional of application Ser. No. 193,211 filed Oct. 27, 1971, now U.S. Pat. No. 3,840,571 of Oct. 8, 1974.

This invention relates to the methods for preparing higher carboxylic acids, and more particularly it relates to preparation of higher branched unsaturated dialkylamino acids.

Said acids can be used as detergents, wetting, foaming and flotation agents, emulsion and suspension stabilizers, special detergents, disinfectants and preservatives.

Dialkylaminoalkylterpenylacetic acids are new compounds which have not been described in special literature.

The compounds have the general formula:

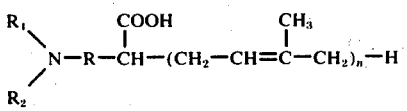

where R is alkylene of 2 to 6 carbon atoms, $R_1$ and $R_2$ are alkyl of 1 to 3 carbon atoms and $n$ is 2 or 3.

These are zwitterionic compounds characterized by surface-active and antibacterial properties.

The specific features of dialkylaminoalkylterpenylacetic acids are their high hydrophilic (they are dissolved and miscible with water in any proportions) and lipophilic properties.

The proposed substances are obtained by a method in which, according to the invention, substituted malonic esters are reacted with alkyl halide. The thus formed ester is saponfied and decarboxylated in vacuum or in a medium of a high-boiling solvent, for example n-nonane, n-decane, cumene, or tetralin.

Terpenylmalonic esters or dialkylaminoalkylmalonic esters are used as said substituted malonic esters, and dialkylaminoalkyl halides or terpenyl halides are used as alkyl halides. The starting components, that is a substituted malonic ester and an alkyl halide taken in equimolar quantities or with excess of a substituted malonic ester, are reacted in the presence of a sufficiently strong base, for example metal sodium, in an inert solvent. Preparation of the substituted malonic esters employed in the present invention may be carried out by generally known methods such as are described in *Organic Reactions*. Vol. IX, Wiley and Sons, pp. 107, 113, 175, 186, 196, 322 and 327 and also *Chemical Abstracts*. Vol. 53, pp. 21788-89 (1959) and Vol. 61, p. 13186 (1964).

The reaction mixture is heated at a temperature at which the given solvent boils.

After the reaction is completed, inorganic salts formed in the reaction are removed, and the reaction product is then isolated by fractionation distillation.

The isolated product is saponified, for example, with an alcoholic solution of an alkali, for example, potassium hydroxide.

The saponification product is then neutralized, for example, with dilute hydrochloric acid. The formed acid is decarboxylated in vacuum or in a medium of a high-boiling solvent, after which the main product is fractionated.

The advantage of our invention is the simplicity of the process for preparing dialkylaminoalkylterpenylacetic acids, the requirement for only a small list of raw materials, and the simplicity of the process equipment.

For a better understanding of the invention for those skilled in the art, the following examples of practical embodiment of the process are given by way of illustration.

EXAMPLE 1

To a boiling mixture of 6.2 g of sodium and 80 ml of xylene, with stirring are added gradually 80.2 g of geranylmalonic ester; the mixture is heated for one hour until all of the sodium is dissolved and then 29–32 g of dimethylaminoethyl chloride (in a solvent or without it) are added at a rate that ensures slight boiling of the reaction mixture. The reaction mixture is then heated with stirring so that the solvent boils until the reaction of a sample to phenolphthalein is neutral. After the mixture is cooled, the formed salt precipitate is dissolved by adding sufficient water, the reaction products are extracted with an organic solvent immiscible with water, for example with xylene. The solvent is then distilled and the residue (dimethylaminoethylgeranylmalonic ester) is fractionated in vacuum. As a result, 42 g of the dimethylaminoethylgeranylmalonic ester are produced. The boiling point of the ester is 178°–179° C/4 mm, $n^{20}$ 1.4720. To the boiling concentrated alcoholic solution of potassium hydroxide taken in excess, are added with stirring 42 g of dimethylaminoethylgeranylmalonic ester, the mixture is heated for one hour, then the alcohol is removed, the residue is dissolved in water and neutralized for example with hydrochloric acid. The isolated dimethylaminoethylgeranylmalonic acid is filtered with suction, washed with water and dried in a vacuum desiccator. As a result, 32 g of dimethylaminoethylgeranylmalonic acid are produced. The melting point of the acid is 145.5° – 146.0° C (with decomposition). The 32 g of dimethylaminoethylgeranylmalonic acid are decarboxylated in a hydrocarbon solvent having a boiling point of 150° C and above, for example in n-decane, after which the formed monocarboxylic acid is purified by fractionation in vacuum. 29 g of dimethylaminoethylgeranylacetic acid are obtained. The melting point of the acid is 183° – 185° C/2 mm, $n^{20}$ 1.4945.

EXAMPLE 2

To a boiling suspension of 11.5 g of sodium in a high-boiling solvent, for example, xylene, with stirring are added 148.2 g of geranylmalonic ester, then a solution of dimethylaminopropyl chloride, prepared from 91 g of hydrochloride in the same solvent is added at a rate that ensures slight boiling of the mixture. The mixture is then heated to boil the solvent until the alkaline reaction to phenophthalein disappears. The reaction mixture is cooled and the precipitate of inorganic salts is dissolved with water, the organic layer containing the reaction products is separated, the aqueous layer is extracted with an organic solvent, the extracts are joined together with the organic bed, the extracting agent and the solvent are distilled and the residue is then fractionated in vacuum. As a result, 117 g of dimethylaminopropylgeranylmalonic ester are obtained. The melting point of the ester is 180° – 185° C/2.5 mm, $n^{20}$ 1.4693. To the boiling solution of 100 g of potassium hydroxide in alcohol are added the 117 grams of dimethylaminopropylgeranylmalonic ester, after which the mixture is heated for one hour, the alcohol is distilled, the residue dissolved in water, the solution neutralized with an acid, for example, with dilute hydrochloric acid, liberated dimethylaminopropylgeranylmalonic acid is separated on a filter, washed with water, and dried in vacuum. The resulting product is 98 g of dimethylaminopropylgeranylmalonic acid; the melting point of the product is 162.5° − 164° C (with decomposition). The 98 g of dimethylaminopropylgeranylmalonic acid are decarboxylated in a boiling hydrocarbon solvent, for example, in tetralin, the tetralin is then distilled and the residue fractionated in vacuum. As a result 53 g of dimethylaminopropylgeranylacetic acid are produced. The boiling point of the acid is 143° C/3 mm, $n^{20}$ 1.4945.

EXAMPLE 3

Not less than 58 g of dimethylaminopropylgeranylmalonic ester are prepared from 122.7 g of dimethylaminopropylmalonic ester, 11.5 g of sodium and 86.4 g of geranyl chloride (as in Example 1) by heating in toluene until the alkaline reaction to phenolphthalein disappears, with subsequent treatment and fractionation in vacuum as described in the previous examples. The boiling point of the ester is 183° − 190° C/3 mm, $n^{20}$ 1.4710. The dimethylaminopropylgeranylmalonic ester is saponified with alkali into dimethylaminopropylgeranylmalonic acid. After filtration and washing with water, moist dimethylaminopropylgeranylmalonic acid is loaded into a flask, dried in vacuum and decarboxylated by heating in vacuum to a temperature over that at which it melts, and the formed dimethylaminopropylgeranylacetic acid is then fractionated in vacuum.

EXAMPLE 4

122.7 g of dimethylaminopropylmalonic ester, 11.5 g of sodium and 86.4 g of geranyl chloride (as in Example 1) are heated in toluene until the alkaline reaction to phenolphthalein disappears; the reaction mixture is then filtered, the solvent is distilled and 58 g of dimethylaminopropylgeranylmalonic ester are obtained after vacuum fractionation. The boiling point of the ester is 183°–190° C/3 mm, $n^{20}$ 1.4710.

Dimethylaminopropylgeranylmalonic acid is prepared by acid saponification of the dimethylaminopropylgeranylmalonic ester, by boiling, for example, with hydrochloric acid, with subsequent neutralization of the hydrochloric acid with a base, for example, with a solution of sodium hydroxide. After filtration and washing with water, the moist dimethylaminopropylgeranylmalonic acid is loaded into a flask and dried in vacuum. The dried acid is decarboxylated by heating in vacuum to a temperature above its melting point and the thus formed dimethylaminopropylgeranylacetic acid is then fractionated in vacuum.

EXAMPLE 5

19.2 g of farnesylmalonic ester, 1.2 g of sodium and dimethylaminopropyl chloride isolated from 9.1 g of the hydrochloride (as in Example 1) are heated in toluene until the alkaline reaction to phenolphthalein disappears, with subsequent distillation in vacuum. As a result, 12 g of dimethylaminopropylfarnesylmalonic ester are obtained. The boiling point of the ester is 214° − 216° C/2 mm, $n^{20}$ 1.4810. The 12 g of dimethylaminopropylfarnesylmalonic ester are saponified with a solution of 16 g of potassium hydroxide in 24 ml of ethyl alcohol and 9.2 g of dimethylaminopropylfarnesylmalonic acid are obtained as a result. The melting point of the acid is 146°–148° C (with decomposition). The acid is then decarboxylated in vacuum by heating to a temperature over its melting point, and 5.2 g of dimethylaminopropylfarnesylacetic acid are produced as a result. The boiling point of the new acid is 227°–290° C/6 mm, $n^{20}$ 1.5007.

EXAMPLE 6

14.82 g of geranylmalonic ester, 1.15 g of sodium and diethylaminoethyl chloride isolated from 8.91 g of the hydrochloride (as in Example 1) are heated in xylene to obtain 10.5 g of diethylaminoethylgeranylmalonic ester, having a boiling point of 192°–195° C/2 mm, $n^{20}$ 1.4688. The diethylaminoethylgeranylmalonic ester is saponified with excess concentrated solution of sodium hydroxide in alcohol to obtain 3.8 g of diethylaminoethylgeranylmalonic acid, which is then decarboxylated in vacuum to yield 2.3 g of diethylaminoethylgeranylacetic acid having a boiling point of 180° − 185° C/1–2 mm, $n^{20}$ 1.4958.

EXAMPLE 7

450.5 g of geranylmalonic ester, 34.9 g of sodium and 227.3 g of diethylaminopropylchloride (b.p., 73°–78° C/20 mm) isolated from 423.3 g of hydrochloride, are heated in toluene to obtain 329.4 g of diethylaminopropylgeranylmalonic ester having a boiling point of 185°–210° C/2 mm, $n^{20}$ 1.4709. The 329.4 grams of diethylaminopropylgeranylmalonic ester are saponified with a concentrated solution of potassium hydroxide in alcohol to prepare 524.7 g of moist diethylaminopropylgeranylmalonic acid. The diethylaminopropylgeranylmalonic acid, either moist or dried, is then decarboxylated in vacuum (after dehydration of the acid in vacuum). 156 g of diethylaminopropylgeranylacetic acid are produced. The boiling point of the acid is 190°–200° C/2 mm, $n^{20}$ 1.4951.

EXAMPLE 8

22.5 g of geranylmalonic ester, 1.74 g of sodium and dipropylaminogexyl chloride isolated from the hydrochloride produced from 18.9 g of dipropylaminohexyl alcohol (b.p., 148°–152° C/17 mm) (as in Example 1) are heated in toluene to prepare 13.3 g of dipropylaminohexylgeranylmalonic ester, having a boiling point of 200°–215° C/2 mm, $n^{20}$ 1.4730. The dipropylaminohexylgeranylmalonic ester is saponified with a concentrated solution of potassium hydroxide in alcohol and neutralized with an acid to obtain dipropylaminohexylgeranylmalonic acid, which is then decarboxylated in vacuum to yield 5.5 g of dipropylaminohexylgeranylacetic acid. The boiling point of the acid is 230° − 236° C/3 mm, $n^{20}$ 1.4938.

We claim:

1. A method for preparing a higher branched unsaturated dialkylamino acid of the formula

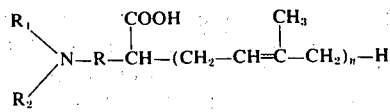

wherein R is alkylene of 2 to 6 carbon atoms, $R_1$ and $R_2$ are lower alkyl of 1 to 3 carbon atoms and $n$ is 2 or 3, which comprises reacting a terpenylmalonic ester with a dialkylaminoalkyl halide, followed by saponifying and decarboxylating the reaction mixture.

2. The method of claim 1 wherein said terpenylmalonic ester is selected from the group consisting of geranylmalonic ester and farnesylmalonic ester.

3. The method of claim 1 wherein said dialkylaminoalkyl halide is selected from the group consisting of dimethylaminoethyl chloride, diethylaminoethyl chloride, dimethylaminopropyl chloride, diethylaminopropyl chloride and dipropylaminohexyl chloride.

4. The method of claim 1 wherein saponification is carried out with a hydrochloric acid solution.

5. The method of claim 1 wherein saponification is carried out with a solution of sodium hydroxide or potassium hydroxide in alcohol.

6. The method of claim 1 wherein decarboxylation is carried out in vacuum.

7. The method of claim 1 wherein decarboxylation is carried out in a high-boiling inert solvent medium.

8. A method for preparing a higher branched unsaturated dialkylamino acid of the formula

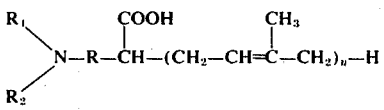

wherein R is alkylene of 2 to 6 carbon atoms, $R_1$ and $R_2$ are lower alkyl of 1 to 3 carbon atoms and $n$ is 2 or 3, which comprises reacting a dialkylaminoalkylmalonic ester with a terpenyl halide, followed by saponifying and decarboxylating the reaction mixture.

9. The method of claim 8 wherein said dialkylaminoalkylmalonic ester is selected from the group consisting of dimethylaminoethylmalonic ester, diethylaminoethylmalonic ester, dimethylaminopropylmalonic ester, diethylaminopropylmalonic ester and dipropylaminohexylmalonic ester.

10. The method of claim 8 wherein said terpenyl halide is selected from the group consisting of geranyl chloride and farnesyl chloride.

11. The method of claim 8 wherein saponification is carried out with a hydrochloric acid solution.

12. The method of claim 8 wherein saponification is carried out with a solution of sodium hydroxide or potassium hydroxide in alcohol.

13. The method of claim 8 wherein decarboxylation is carried out in vacuum.

14. The method of claim 8 wherein decarboxylation is carried out in a high-boiling inert solvent medium.

* * * * *